United States Patent [19]

Cooper et al.

[11] Patent Number: 5,224,947
[45] Date of Patent: Jul. 6, 1993

[54] SOFT, READILY EXPANDABLE VACUUM BELL ASSEMBLY

[76] Inventors: Richard N. Cooper, One Jefferson Pkwy., Apt. 25, Lake Oswego, Oreg. 97035; Lawrence M. Smith; Emily M. Smith, both of 18989 Couch Market Rd., Bend, Oreg. 97708

[21] Appl. No.: 781,089

[22] Filed: Oct. 21, 1991

[51] Int. Cl.⁵ .................... A61B 17/00; A61M 1/00
[52] U.S. Cl. .................... 606/123; 606/119; 606/121
[58] Field of Search .............. 606/1, 119, 121–123; 604/902

[56] References Cited

U.S. PATENT DOCUMENTS

| 2,194,989 | 3/1940 | Torpin | 606/123 |
| 2,702,038 | 2/1955 | Uddenberg et al. | 606/123 |
| 2,917,050 | 12/1959 | Kenyon | 606/123 |
| 3,202,152 | 8/1965 | Wood et al. | 606/123 |
| 3,207,160 | 9/1965 | Heyns | 606/123 |
| 3,765,408 | 10/1973 | Kawai | 606/123 |
| 3,782,385 | 1/1974 | Loyd | 604/74 |
| 3,794,044 | 2/1974 | Vennard et al. | 606/123 |
| 5,019,086 | 5/1991 | Neward | 606/123 |
| 5,071,403 | 12/1991 | Larsson | 604/74 |

FOREIGN PATENT DOCUMENTS

| 1123432 | 2/1962 | Fed. Rep. of Germany | 606/123 |
| 3138589 | 4/1983 | Fed. Rep. of Germany | 606/123 |
| 1087487 | 2/1955 | France | 606/119 |
| 0141257 | 1/1960 | U.S.S.R. | 606/123 |
| 8906112 | 7/1989 | World Int. Prop. O. | 606/123 |

Primary Examiner—Stephen C. Pellegrino
Assistant Examiner—Glenn Dawson
Attorney, Agent, or Firm—Marger, Johnson, McCollom & Stolowitz

[57] ABSTRACT

The subject invention is directed to a vacuum bell assembly for assisting an obstetrician in controlling and accurately attaching the cranial traction cup to a predetermined attachment point on the infant's head during childbirth. The handle is typically designed to offer a measure of flexibility when pulling traction is applied during use so that even if the obstetrician is not pulling exactly on a straight axis, the cup will not be disengaged from it's attachment to the fetal scalp thereby interrupting the delivery process. The vacuum bell assembly has a cranial extraction cup fabricated from a soft, readily expandable material. This reduces the chances of injury to the fetal scalp and to the tender tissue of the vaginal walls in the birth canal. The cranial traction cup defines an internal attachment chamber having an outer opening for attaching the cup to a portion of an infant's head located within the internal attachment chamber. The nature of the material from which the cup is fabricated allows the cup rim to expand and fit the head of each individual infant. In this way, when suction forces from within the internal attachment chamber during use are applied to the infant's head, the cranial traction cup assists in withdrawing the infant from its mother's birth canal during childbirth. Because a proper fit on each infant's head is ensured by the cup design, no vacuum leaks will occur when subatmospheric pressure is applied. This enables an obstetrician to pull in an effective and efficient manner to advance the infant's head through the birth canal.

14 Claims, 2 Drawing Sheets

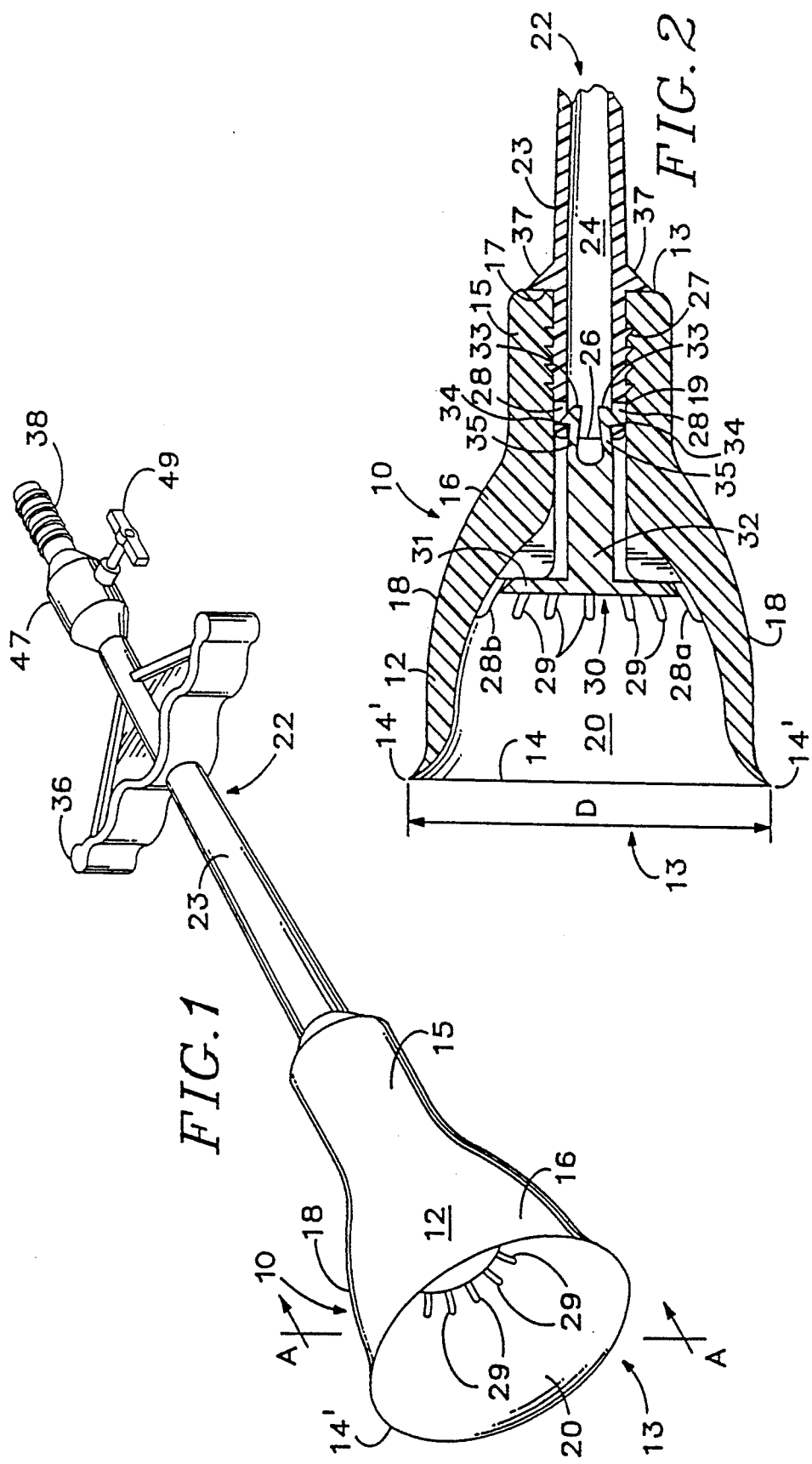

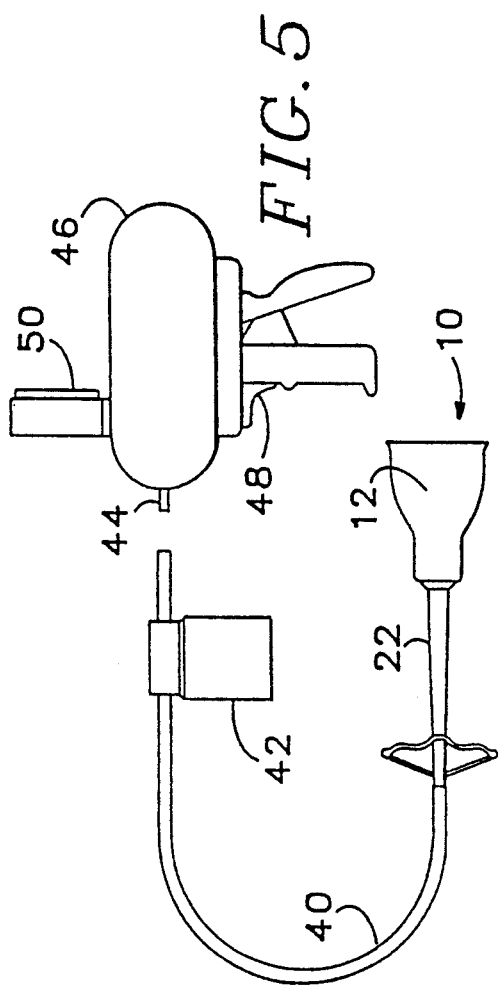
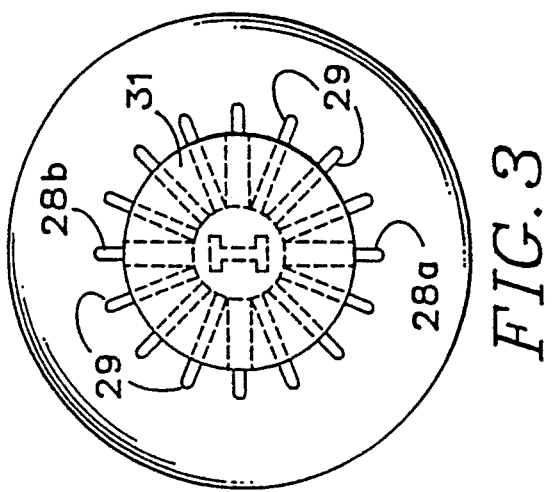
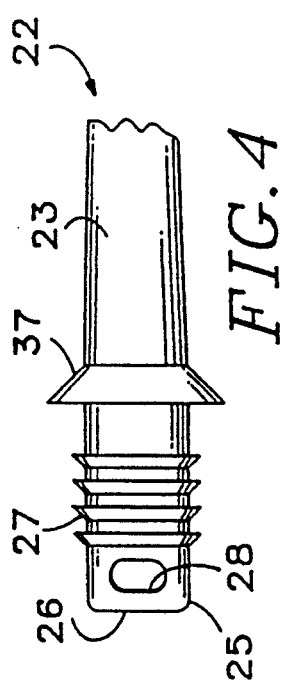

SOFT, READILY EXPANDABLE VACUUM BELL ASSEMBLY

BACKGROUND OF INVENTION

The present invention generally relates to a soft, readily expandable vacuum bell assembly and, specifically, to a soft, readily expandable vacuum bell assembly for obstetrical use in the delivery room in an effective and efficient manner.

In some instances during the birth of a child a completely natural birthing process is not possible. Therefore, assistance must be rendered by the attending physician in order for the child to be delivered from the birth canal. In the past, forceps and other like devices which tend to be bulky and hard to handle were employed to provide assistant during the course of delivery. These devices often caused injury to the mother and child. Vacuum extractors have also been employed in vacuum extraction assemblies. In 1953 the Malmstrom metal cup was introduced.

In 1965, a vacuum extraction cup made of polyethylene was first marketed. These vacuum bells or cups are of the type hereafter described in U.S. Pat. No. 3,202,152 which are used during infant delivery to provide assistance in maneuvering the baby's head in the birth canal. In this way, a proper presentation of the baby is made to the obstetrician thereby facilitating the birthing process. The vacuum bell, which is operated by applying subatmospheric pressure, is secured to the head of a child and then manipulated properly to augment the parturient forces exerted by the mother during the delivery process and withdraw the child from the birth canal. By using the vacuum forces exerted by the bell assembly, the amount of effort needed to be expended by the mother is reduced, the expulsion of the baby from the birth canal can be more easily facilitated, and the time the baby needs to spend in the delivery process is greatly reduced.

In U.S. Pat. No. 3,202,152, a vacuum-assisted device for attaching to the head of a child is provided which includes an elongated hollow stem is joined to a vacuum cup, and is used to manipulate the cup during delivery. The device is made of a stiff polymeric material which is easily cleaned and sterilized in the event that such should be reused. The stiff vacuum bell assembly employs a wide range of pulling forces, in the form of a subatmospheric vacuum, accompanied with proper positioning, to be employed in the manipulation of the device. Many obstetricians, however, do not like to use this device because they perceive that the use of a vacuum-assisted device fabricated of a stiff polymeric material is a safety problem which substantially increases the chance of injury to the infant during delivery.

To avoid traumatizing the baby's scalp during the delivery process, great care must be taken to balance the need to maintain contact with the baby's head while avoiding pulling the scalp into the vacuum bell by the use of excessive vacuum. Thus, some cranial cups include a deflector shield or plate, placed across the bottom of the bell and over the exhaust hole, so that as the bell is drawn down onto the baby's head by the external air pressure, the scalp will come to rest against the plate, providing an extended area over which to distribute the pressure. Further, existing vacuum bells usually use an exhaust tube extending axially from the bell itself to a source of vacuum. The exhaust tube can include a handle for controlling the use of the vacuum bell during the birthing process. For example, the natural tendency during use of a vacuum bell such as described in U.S. Pat. No. 3,202,152 is to bend the handle to obtain a better grip thereon. This will often lift one side of the cranial cup from the baby's scalp. This breaks the vacuum seal, requiring the cup to be reseated, and the vacuum redrawn, taking precious time from the limited amount permitted to avoid traumatizing the baby.

Accordingly, another prior art vacuum-operated device has been developed which overcomes some of the problems described above regarding the use of vacuum bell assemblies fabricated of stiff polymeric. In U.S. Pat. No. 3,765,408, a soft obstetric vacuum cup and stem assembly is used for assisting child delivery. The obstetric cup which comprises a cup-shaped body made of an elastic material, a plurality of recessed portions formed around the upper inner periphery of the cup-shaped body in a spaced apart relationship, a suction tube communicating with the bottom of the cup-shaped body and extending outwardly therefrom, and a plurality of passages formed through the wall of the cup-shaped body to communicate the recessed portions with the suction tube. The cup is configured with a hemispherically-shaped outer and inner wall portion, the inner wall portion being inwardly curved at its outer edge.

Therefore, a need exists for a soft, readily expandable vacuum bell assembly for obstetrical use in the delivery room in an effective and efficient manner, which provides a high degree of safety to a baby during the birthing process, but at the same time exhibits a sufficient amount of attachment to the head of the infant which augments the parturient forces exerted by the mother so that the delivery process can be affected.

SUMMARY OF THE INVENTION

Applicants have studied the above prior art vacuum cup designs, and have determined that a combination of specific design features and materials of construction will provide a vacuum extractor system which will offer a much more effective delivery, while at the same time giving maximum consideration to the safety and comfort of the infant and the mother. Applicants have also met the above-described needs existing with respect to a vacuum bell assembly of obstetrical use in the delivery room. More specifically, the subject vacuum bell assembly provides for a substantial amount of safety to a baby and mother during the birthing process but at the same time exhibits a sufficient degree of attachment to the head of the infant which will augment the parturient forces exerted by the mother in the birth canal and will facilitate the delivery process.

Applicants have discovered that in order to facilitate the birthing process in an effective and efficient manner, the use of a one-piece, soft, readily expandable vacuum bell assembly, such as set forth in U.S. Pat. No. 3,765,408 cannot be employed because it has several inherent design problems. For instance, a one-piece, soft, readily expandable vacuum bell assembly presently being manufactured by Dow Corning is sold under the trademark "SILASTIC". The SILASTIC product, which is similar in design to the vacuum cup of U.S. Pat. No. 3,765,408, has an inner lip which is curved inwardly, the vacuum cup forming a minimum cross-section area for attachment to the head of an infant. This causes the rim to turn inward when negative vacuum pressure is applied thereto. Thus, the prior art vacuum cup was observed to collapse inwardly when subjected to negative vacuum pressure under simulated use conditions, thereby substantially further reducing the cross-sectional area of contact in use between the vacuum cup and the head of the infant, as compared to the cross-section area of the vacuum cup when not in use. This in turn significantly substantially reduces the attachment capabilities of the vacuum cup with respect to the infant being delivered. Therefore, in many instances, the SILASTIC vacuum cup is ineffective in assisting an obstetrician in facilitating the successful completion of the delivery process because the pulling power of the SILASTIC vacuum cup is not sufficient to augment the parturient forces exerted by the mother in the birthing canal. In such cases, use of forceps is employed or a C-section is performed by the obstetrician to complete the delivery. Furthermore, applicants have discovered that since the SILASTIC vacuum cup is a one-piece construction, and therefore totally fabricated of a soft, pliable silicone rubber, it is difficult to control the vacuum cup for accurate attachment to a predetermined attachment point on the head of the infant during delivery.

More specifically, the subject invention is directed to a vacuum bell assembly for assisting an obstetrician in controlling and accurately attaching the cranial traction cup to a predetermined attachment point on the infant's head during childbirth. The handle is typically designed to offer a measure of flexibility when pulling traction is applied during use so that even if the obstetrician is not pulling exactly on a straight axis, the cup will not be disengaged from it's attachment to the fetal scalp thereby interrupting the delivery process. The vacuum bell assembly comprises a cranial extraction cup fabricated from a soft, readily expandable material. This reduces the chances of injury to the fetal scalp and to other tender tissue of the vaginal walls in the canal. The cranial traction cup defines an internal attachment chamber having an outer opening for the attaching the cup to a portion of an infant's head located within the internal attachment chamber. The nature of the material from which the cup is fabricated allows the cup rim to expand and fit the head of each individual infant. In this way, when suction forces from within the internal attachment chamber during use are applied to the infant's head, the cranial traction cup assists in withdrawing the infant from its mother's birth canal during childbirth. Because a proper fit on each infant's head is ensured by the cup design, no vacuum leaks will occur when subatmospheric pressure is applied. This enables an obstetrician to pull in an effective and efficient manner to advance the infant's head through the birth canal.

The vacuum bell assembly is specifically fabricated of different structural materials. The cup portion typically includes a cranial traction cup which is fabricated of a soft, readily expandable material. Typically, the soft, readily expandable material from which the cranial traction cup is fabricated comprises a silicone rubber. As for the semi-rigid extraction handle, it is preferably fabricated of a "low density" polyolefin material. This type of material ensures that no sharp edges or hard surfaces will contact the delicate scalp tissue of the infant or the tender tissue of the mother's vaginal walls and birth canal. The physicians can easily compress the rim of the subject cup for insertion during delivery. Once inserted, the cup rim will regain its original shape and allow the cup opening to fit easily over the infant's head.

Conversely, the semi-rigid extension handle encourages and enables the physician to pull in a straight path during delivery. This is the most effective and efficient delivery procedure. When the handle is made of a soft material, such as in the Silastic cup structure, the physician tends not to pull in a straight line path. This creates uneven traction on the cup, and can cause the cup to become detached from the scalp of the infant during the delivery process.

The vacuum bell assembly of the present invention is designed as a two-piece assembly which are connected one to another. Thus, the attachment end of the extraction handle will preferably extend into a connection joint created in the cranial traction cup. It will then further extend to the point of attachment to the deflector shield forming an interlocking integral structure which will not pull apart during use. In this preferred configuration, a space is created behind the deflector shield. This ensures that during the application of negative vacuum pressure, even if the infant's scalp tissue contacts the deflector shield, the vacuum pressure will not be shut off, and the vacuum in the cranial traction cup will be sufficient to effect delivery of the child.

A source of subatmospheric pressure is also provided in communication with the internal attachment chamber for creating suction forces within the internal attachment chamber. The outer opening of the cranial traction cup has a diameter, when suction forces from within the internal attachment chamber during use are applied to the infant's head, which is at least equal to the diameter of the outer opening of the cranial traction cup during non-use. Non-use is defined as when substantially no suction forces from within the internal attachment chamber are applied to the infant's head. This structural design of the vacuum bell assembly facilitating a sufficient attachment of the cranial traction cup to the head of an infant which will augment the parturient forces exerted by the mother in the birth canal during the delivery process.

The vacuum bell assembly typically includes a cranial traction cup which is fabricated of a soft readily expandable material. Typically, the soft readily expandable material comprises a polymeric material from which the cranial traction cup is fabricated, preferably a silicone rubber. As for the semi-rigid extraction handle, it is preferably fabricated of a "low density" polyolefin material.

Regarding the structure of the vacuum bell assembly of the present invention, the semi-rigid extraction handle comprises an exhaust tube assembly including an internal bore, and the source of subatmospheric pressure is in communication with the internal attachment chamber through the internal bore. The exhaust tube assembly is designed to be of a specific length. It is long enough to provide a good feel and balance, and to enable the obstetrician to position the vacuum cup far enough into the birth canal to reach a fetal head which may be at high station, such as a case involving a high second twin or mid pelvic station.

Moreover, the outer opening of the internal attachment chamber has an outwardly-flared configuration. The flared rim of the cup is encouraged, during placement on the baby's scalp, to move into proper position and not buckle inwardly as is the case with the prior art soft, expandable vacuum bells. Preferably, the semi-rigid stem and extraction handle is connected to the cranial traction cup by an interlocking deflector shield. The deflector shield, which protects the infant's scalp from being pulled into the vacuum tube while it engages the cranial traction cup, with interlocking connectors to the semi-rigid extraction handle to form an integral vacuum bell assembly.

A method for assisting an obstetrician in withdrawing an infant from a mother's birth canal during childbirth is also set forth in the present invention. The subject method generally includes the steps of providing a cranial traction cup fabricated from the soft, readily expandable material, the cranial traction cup defining an internal attachment chamber having an outer opening, and a semi-rigid extraction handle connected to the soft readily expandable cranial traction cup. Next, suction forces are created within the internal attachment chamber by introducing a subatmospheric pressure to the internal attachment chamber. The doctor then controls and accurately attaches the cranial traction cup to a predetermined attachment point on the infant's head during childbirth by locating the infant's head within the internal attachment chamber so that when suction forces from within the internal attachment chamber during use are applied to the infant's head. As stated above, the outer opening of the cranial traction cup has a diameter, when suction forces from within the internal attachment chamber during use are applied to the infant's head, which are at least equal to the diameter of the outer opening of the traction cup during a non-use condition The infant can then be withdrawn from its mother's birth canal during the delivery process.

The forgoing and other objects, features and advantage of the invention will become more readily apparent from the following detailed description of a preferred embodiment which proceeds with reference to the drawing.

BRIEF DESCRIPTION OF THE DRAWINGS

FIG. 1 is a perspective view of a vacuum bell assembly of the present invention which includes a vacuum cup, an exhaust tube assembly, including a vacuum release valve, and a deflector plate.

FIG. 2 is an enlarged, cross-sectional view of the vacuum bell assembly of FIG. 1, taken along lines 2—2.

FIG. 3 is an enlarged, front end view of the vacuum bell assembly of FIG. 2 showing the internal surface 20 of the vacuum bell.

FIG. 4 is an enlarged, fragmentary side view of the exhaust tube assembly showing an alternative version of the attachment portion therefore without a vacuum release valve.

FIG. 5 is a schematic view of the vacuum bell assembly of FIG. 1 and an associated vacuum source operational system.

DETAILED DESCRIPTION OF THE PRESENT INVENTION

Referring now to FIGS. 1 and 2, the birthing assistance vacuum bell 10 of the present invention comprises a generally bell-shaped cranial traction cup 12, having a hollow central chamber 13 including an outer opening 14, a dome portion 16, a neck portion 15, and external and internal surfaces 18 and 20. The neck portion 15 has disposed at its top portion an opening 17 which is in communication with a hollow central passageway 19, which in turn is in communication with central chamber 14. The outer opening 14 is defined by an outer lip portion 14' which is outwardly flared to facilitate a sufficient minimum amount of attachment of the vacuum cup 12 to the head of an infant which will augment the parturient forces exerted by the mother in the birth canal during the delivery process. The form of attachment of the vacuum cup 12, which will hereinafter be discussed, is shown in FIG. 3.

Dome portion 16 includes inwardly angled, substantially equidistantly-spaced support portions 28a–28b joined to and extended outwardly from internal surface 20. Support portions 28a and 28b are of substantially triangular configuration. Dome portion 16 further includes a plurality of substantially equidistantly-spaced ribs 29 which are joined to and extended outwardly from internal surface 20. The ribs 29 are also in a substantially uniformly spaced relationship with each other.

Cranial traction cup 12 is fabricated of a soft, flexible, readily-expandable material. For example, the cup 12 can be fabricated from a silicone rubber. This material is a clear, medical-grade polymeric material. The diameter "D" of outer lip portion 14' during use (see FIG. 2), with a vacuum source applied thereto through exhaust tube assembly 22, in engagement with the head of a baby, is at least equal to the diameter "D" of outer lip portion 14' when not in use with no substantial vacuum applied thereto through tube 22.

Connected to the cranial traction cup 12, within hollow central passageway 19, and extending axially away therefrom, is exhaust tube assembly 22 which is employed as the extraction handle 36 during the birthing operation. Exhaust tube assembly 22 comprises a tubular member 23 having an internal bore 24 which extends throughout the entire length thereof. This assembly 22 is made of a semi-rigid polymeric material. A first end of the exhaust tube assembly 22 is connected to cranial traction cup 12 within hollow central passageway 19, and a second end of exhaust tube assembly 22, having a vacuum release valve 47 installed therein in the preferred embodiment of FIG. 1, is in communication with an external source of vacuum via flexible tubing 40. The vacuum release valve 47 is a safety device which can be provided to permit physicians using the birthing assistance vacuum bell 10 the option of quickly and immediately releasing vacuum pressure as needed during the birthing process. The internal working mechanism (not shown) of vacuum release valve 47 can comprise, for example, a semi-rigid plastic housing, a release port and a rubber stopper. The release valve 47 is actuated by thumb release button 49 and can be controlled by the amount of pressure applied thereto. The exhaust tube assembly 22, in any case, has at it's second end attachment barbs 38 to facilitate connection of the exhaust tube assembly 22 to exhaust tubing 40, and further includes extraction handle 36 for enhancing the extraction process. The handle 36 preferably extends transversely to tubular member 23 and is designed to be fully gripped by an obstetrician during use being a specific width which fits comfortably into a closed palm when the obstetrician grasp the device for use during the delivery process. More specifically, the traction handle 36 is designed with finger resting grooves on the underside of the handle to fit comfortably and to provide a non-slip grip for better control when manipulating the cup 12 during use. A vacuum release valve 47 is located between attachment barbs 38 and traction handle 36, and includes a thumb release bottom 49 which when inwardly depressed by an obstetrician will instantly release the subatmospheric pressure in the system. The vacuum valve 47 is designed to provide the obstetrician with a means of vacuum release without relying on an assistant who is operating the vacuum pump. This provides an additional measure of safety during the delivery process.

The first end of exhaust tube assembly 22 comprises an end portion 25 having an exit orifice 26 which forms the end of the internal bore 24. The first end of exhaust tube assembly 22 also includes a barbed portion 27 which facilitates attachment of exhaust tube assembly 22 within hollow central passageway 19. This ensures continued attachment of the exhaust tube assembly 23 to the cranial traction cup 12 during the delivery process. Located in tubular member 23 between exit orifice 26 and barbed end portion 27 are a pair of openings 28 which are equidistantly spaced one from the other and which is in communication with internal bore 24. Also located in tubular member 23, adjacent to and on the other side of barbed end portion 27, is a retaining shoulder 37 which when the exhaust tube assembly 22 is fully located within hollow central passageway 19, is in engagement with the top portion 13 of the neck portion 15 for restraining the movement of assembly 22 within hollow central passageway 19.

Mounted inside of cup 12 is a deflector shield assembly 30 which fulfills two major purposes. First, it is designed to prevent the fetal scalp from extending into the vacuum port thereby shutting off the source of subatmospheric pressure from reaching space 20 of the vacuum bell. The inner portion of assembly 30 is deliberately positioned within the shoulder at the upper end of the vacuum bell, but below the neck joint where the semi-rigid extraction handle 36 connects to the cup 12. In this way an additional space is formed for the passing of the subatmospheric pressure should the fetal scalp fill the vacuum bell below the inner portion of the assembly. The deflector shield assembly 30 comprises a flat, annular disk portion 31 and a stem portion 32, joined at one end to the midpoint of the annular disk portion 31, and extending in a direction normal to flat surface.

There is a specially designed interlocking mechanism which joins the cup 12 and the exhaust tube assembly 22 so that they cannot accidentally pull apart during the delivery process, without requiring the use of glue. This interlocking design also allows the assembly 30 to be suspended in the shoulder of the cup 12 while providing an open tube 24 to allow subatmospheric pressure to reach the space 20 of the vacuum bell for the reasons discussed above. The mechanism is located at the other end of stem portion 32 and comprises a generally U-shaped connector forming a pair of outer arms 33, each of the arms 33 having an ear 34 at each of its outer ends. Once exhaust tube assembly 22 is in position within hollow central passageway 19, deflector shield assembly 30 is positioned within chamber 13 by moving stem portion 32 into hollow central passageway 19 and arms 32 through exit orifice 26 and into internal bore 24. Ears 34 are moved inwardly by compressive action toward each other as stem portion 32 is introduced into passageway 19. When outwardly-extending ears 34 moved to a point adjacent to opening 27, ears 34 are moved to an extended position within the confines of openings 28 and connecting deflector shield assembly 30 to exhaust tube assembly 22.

In this position, the outer surface of annular disk portion 31 is engaging ribs 29 and the inner flat surface of annular disk portion 31 is engaging inner surface 20. Deflector shield 30 performs several functions, as hereinafter explained more fully. Deflector shield 30 spreads the air current of the exhausting gas around its lengthy circumference, reducing the velocity thereof and tending to reduce the amount of particulate and liquid material which might other wise be drawn into the vacuum system. Further, the surface thereof is smooth thereby reducing the possibility of lacerating the scalp of the baby, as previously explained in connection with the discussion of existing vacuum bells.

In operation, as shown in FIG. 5, a typical delivery system is provided in which the second end of exhaust tube assembly 22 of birthing assistance vacuum bell 10 is connected to one end of a predetermined length of conventional medical grade flexible tubing 40. Next, the other end of the tubing is attached to a standard fluid trap 42 to protect the vacuum equipment from contamination. The fluid trap 42 is then connected to the nipple 44 of a vacuum pump 46, such as the Model No. 101A manufactured by Challenge Manufacturing, Inc. of Tigard, Oreg. The vacuum pump 46 includes a vacuum trigger release 48 and a vacuum gauge 50. Vacuum pump 46 is the source of vacuum.

The vacuum pressure of the vacuum pump 46 is checked by pumping vacuum with the cup 12 pressed to the gloved palm of the obstetrician. The gauge needle of vacuum gauge 50 should remain steady during the pressure testing operation. Then, the fetal presentation and position is examined. If the delivery is to be made vaginally, the baby's scalp is cleaned and the cup 12 is gently inserted into the vagina where it is positioned over the occiput of the baby's head. The negative pressure is then raised to 4" Hg to initiate adhesion. At the onset of contraction, the negative pressure is rapidly raised to 15"–23" Hg. and traction is begun. Extraction by the doctor is then done along the pelvic axis in harmony with the contractions. When the contractions stop, the vacuum is reduced to 4" Hg. The above increase and decrease of the negative pressure in combination with the extractive action is continued until the head is drawn over the perineum and delivery of the head is complete. At that time, the head is delivered.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

We claim:

1. A vacuum bell assembly for assisting an obstetrician in withdrawing an infant's head from a mother's birth canal during childbirth, which comprises a cranial extraction cup fabricated from a soft, readily expandable material, said cranial extraction cup defining an internal attachment chamber having an outer opening for attaching the cranial extraction cup to a portion of an infant's head located within said internal attachment chamber, said outer opening of the internal attachment chamber having an outwardly-flared configuration, such that when suction forces from within said internal attachment chamber during use are applied to said infant's head, said cranial extraction cup assists in withdrawing the infant's head from its mother's birth canal during childbirth;

a semi-rigid stem and extraction handle connected to the soft, readily expandable cranial traction cup for assisting an obstetrician in controlling and accurately attaching the cranial traction cup to a predetermined attachment point on the infant's head during childbirth; and a source of subatmospheric pressure in communication with the internal attachment chamber for creating suction forces within said internal attachment chamber;

whereby when suction forces from within said internal attachment chamber during use are applied to said infant's head, said outer opening of said cranial traction cup has a diameter which is at least equal to the diameter of said outer opening of said cranial traction cup during non-use when substantially no suction forces from within said internal attachment chamber are applied to said infant's head, thereby facilitating a sufficient attachment of the cranial traction cup to the head of an infant which will augment the parturient forces exerted by the mother in the birth canal during the delivery process.

2. The vacuum bell assembly of claim 1, wherein said cranial traction cup is fabricated of a soft readily expandable polymeric material.

3. The vacuum bell assembly of claim 2, wherein said soft readily expandable polymeric material comprises a silicone rubber.

4. The vacuum bell assembly of claim 1, wherein said extraction handle is fabricated of a semi-rigid polyolefin material.

5. The vacuum bell assembly of claim 1, wherein said semi-rigid extraction handle comprises an exhaust tube assembly including an internal bore, and said source of subatmospheric pressure is in communication with said internal attachment chamber through said internal bore.

6. The vacuum bell assembly of claim 1, wherein said cranial traction cup and said semi-rigid stem and extraction handle are attachable and detachable with respect to each other, and when attached form an integral vacuum bell assembly.

7. The vacuum bell assembly of claim 6, wherein said semi-rigid stem and extraction handle is connected to said cranial traction cup by a deflector shield assembly including interlocking connector means, said deflector shield assembly protecting the infant's scalp from being drawn into said vacuum port thereby shutting off the source of vacuum.

8. A method for assisting an obstetrician in withdrawing an infant's head from a mother's birth canal during childbirth, which comprises providing a cranial traction cup fabricated from a soft, readily expandable material, said cranial traction cup defining an internal attachment chamber having an outer opening, said outer opening of the internal attachment chamber having an outwardly-flared configuration and a semi-rigid stem and extraction handle connected to the soft readily expandable cranial traction cup;

creating suction forces within said internal attachment chamber by introducing a subatmospheric pressure to said internal attachment chamber;

controlling and accurately attaching the cranial traction cup to a predetermined attachment point on the infant's head during childbirth, by locating the infant's head within said internal attachment chamber so that when suction forces from within said internal attachment chamber during use are applied to said infant's head, said outer opening of said cranial traction cup has a diameter which is at least equal to the diameter of said outer opening of said traction cup during non-use, when substantially no suction forces from within said internal attachment chamber are applied to said infant's, thereby facilitating at least a sufficient attachment of the cranial traction cup to the head of an infant which will augment parturient forces exerted by its mother in the birth canal during the delivery process; and withdrawing the infant's head from a mother's birth canal during childbirth employing said cranial traction cup thereby assisting an obstetrician during the delivery process.

9. The method of claim 8, wherein said cranial traction cup is fabricated of a soft, readily polymeric expandable material.

10. The method of claim 9, wherein said soft, readily expandable material comprises a silicone rubber.

11. The method of claim 8, wherein said semi-rigid extraction handle is fabricated of a semi-rigid polyolefin material.

12. The method of claim 8, wherein said semi-rigid extraction handle comprises an exhaust tube assembly including an internal bore, and said source of subatmospheric pressure is in communication with said internal attachment chamber through said internal bore.

13. The vacuum bell assembly of claim 8, wherein said cranial traction cup and said semi-rigid stem and extraction handle are attachable with respect to each other, and when attached form an integral vacuum bell assembly.

14. The vacuum bell assembly of claim 13, wherein said semi-rigid stem and extraction handle is connected to said cranial traction cup by a deflector shield assembly including interlocking connector means, said deflector shield assembly protecting the infant's scalp from being drawn into said vacuum port thereby shutting off the source of vacuum.

* * * * *